United States Patent [19]
Chen

[11] Patent Number: 5,507,838
[45] Date of Patent: Apr. 16, 1996

[54] ARTIFICIAL FOOT WITH MEMBERS TO HELP WEARER MAINTAIN STEADY BALANCE

[76] Inventor: Sen-Jung Chen, No. 236, Sec. 3, Ho-Ping W. Rd., Taipei City, Taiwan

[21] Appl. No.: 198,177

[22] Filed: Feb. 17, 1994

[51] Int. Cl.⁶ ........................................................ A61F 2/66
[52] U.S. Cl. ................................................. 623/55; 623/53
[58] Field of Search ............................... 623/55, 53, 52, 623/47–51, 38

[56]  References Cited

U.S. PATENT DOCUMENTS

| | | | |
|---|---|---|---|
| 61,780 | 2/1867 | Watson | 623/53 X |
| 969,196 | 9/1910 | Rowley | 623/49 |
| 4,306,320 | 12/1981 | Delp | 623/48 X |
| 4,499,613 | 2/1985 | Yarrow | 623/48 |
| 4,652,266 | 3/1987 | Truesdell | 623/53 |
| 4,721,510 | 1/1988 | Cooper et al. | 623/55 |
| 5,062,859 | 11/1991 | Naeder | 623/55 |
| 5,156,632 | 10/1992 | Wellerhaus | 623/55 |
| 5,376,139 | 12/1994 | Pitkin | 623/51 |

FOREIGN PATENT DOCUMENTS 0262319  1/1970  U.S.S.R. .................... 623/47

OTHER PUBLICATIONS

Hosmer Dorrance Corporation Quantun Foot Brochure.

*Primary Examiner*—David H. Willse
*Attorney, Agent, or Firm*—Ladas & Parry

[57] ABSTRACT

An artificial foot includes a foot-shaped casing that has an open top, a closed bottom, a toe portion, a heel portion and a positioning projection that is formed in the casing and that extends upwardly from the closed bottom. A flexible muscle member is disposed in the casing and has an upwardly protruding curved intermediate section mounted to the positioning projection, and first front and rear sections that respectively extend from the intermediate section frontwardly and rearwardly into the toe and heel portion. A rigid stop member has a weight bearing section that covers the open top of the casing, a curved bottom part riding on the intermediate section of muscle member, and a second front section that extends downwardly and frontwardly into the toe portion so as dispose the same above the first front section of the muscle member. A second rear section of the stop member extends into the heel portion so as to dispose the same above the second rear section of the muscle member.

4 Claims, 4 Drawing Sheets

ARTIFICIAL FOOT WITH MEMBERS TO HELP WEARER MAINTAIN STEADY BALANCE

BACKGROUND OF THE INVENTION

1. Field of the Invention

The invention relates to an artificial foot, more particularly to an artificial foot which can provide steady balance and which can limit bending movement of the same during a walking or running action.

2. Description of the Related Art

FIG. 1 shows a conventional substantially S-shaped artificial foot that includes a weight bearing top portion 1 which is to be worn by an amputee so as to receive and transmit the weight of the amputee, a bottom portion 12, a toe portion 11 and a heel portion 10. Although the conventional artificial foot can provide a relative stability while walking, it fails to prevent further upward bending of the toe portion 11 relative to the top portion 1. As a result, the amputee wearing the conventional artificial foot may lose his balance and fall to the ground in the event that the toe portion bends beyond a limited degree.

Referring to FIG. 2, another type of conventional artificial foot is shown to comprise a horizontal foot portion 2, a vertical support portion 20 and a curved intermediate portion 21 which interconnects integrally the horizontal foot portion 2 and the vertical support portion 20. The vertical support portion 20 is fitted on the stump of an amputee. As illustrated by the arrows in FIG. 3, the conventional artificial foot has a relative flexibility due to the material from which it is made. Thus, in the event that the amputee bends beyond a limited range, the amputee can lose his balance and fall to the ground easily.

SUMMARY OF THE INVENTION

Therefore, the objective of the present invention is to provide an artificial foot which is clear of the above mentioned drawback and which can provide stability so as to enable an amputee who wears the same to walk and act like an ordinary man and so as to prevent the amputee from falling during of bending action.

Accordingly, an artificial foot of the present invention includes an elongated foot-shaped casing that has an open top, a closed bottom, a toe portion, a heel portion and a positioning projection which is formed in the casing and which extends substantially upward from the closed bottom. A flexible muscle member is disposed inside the foot-shaped casing and includes an upwardly protruding curved intermediate section which is mounted to the positioning projection, and first front and rear sections which respectively extend forwardly and rearwardly from the curved intermediate section into the toe and heel portions. A stop member includes a weight bearing section which is disposed so as to cover the open top of the foot-shaped casing. The weight bearing section has a curved bottom part superimposed and mounted to the curved intermediate section of the flexible muscle member, a second front section that extends from the curved bottom part downwardly and frontwardly into the toe portion so as to be disposed above the first front section of the flexible muscle member to prevent further bending movement of the latter relative to the second front section of the stop member when the first front section of the flexible muscle member is bent by application of pressure. The stop member further has a second rear section which extends downwardly and rearwardly from the curved bottom part between the weight bearing section and the first rear section of the muscle member so as to dispose the same above the latter to prevent further bending movement of the first rear section of the muscle member relative to the weight bearing section when the heel portion is compressed.

In the preferred embodiment, a friction reducing piece in the shape of a cylinder is provided between the muscle member and the positioning projection of the foot-shaped casing in order to prolong the useful life of the artificial foot. The friction reducing piece serves as an abutment member and prevents direct contact between the positioning projection and the muscle member, thereby avoiding the untimely ruin which is caused by constant pivotal action of the muscle member relative to the positioning projection.

The second front section of the stop member is further provided with an abutting spacer to abut against the first front section of the muscle member when the latter is bent upward.

The stop member is made from a substantially rigid material and can stop the further bending action of the flexible muscle member so that the amputee who wears the artificial foot can have a steady balance to minimize the risk of falling.

BRIEF DESCRIPTION OF THE DRAWINGS

Other features and advantages of the present invention will become more apparent in the following detailed description of the preferred embodiment with reference to the accompanying drawings, in which.

DETAILED DESCRIPTION OF THE PREFERRED EMBODIMENT

Figure 1:
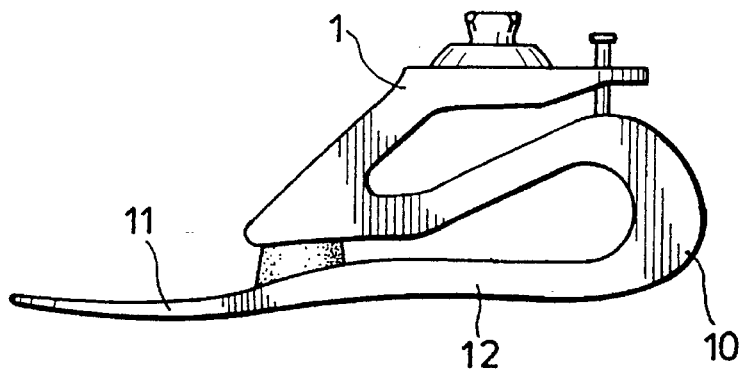
FIG. 1 shows a side view of a conventional artificial foot.
Figure 2:
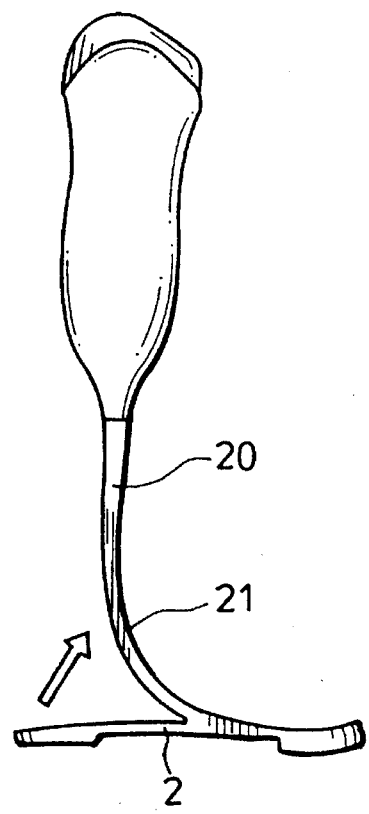
FIG. 2 shows a side view of another conventional artificial foot.
Figure 3:
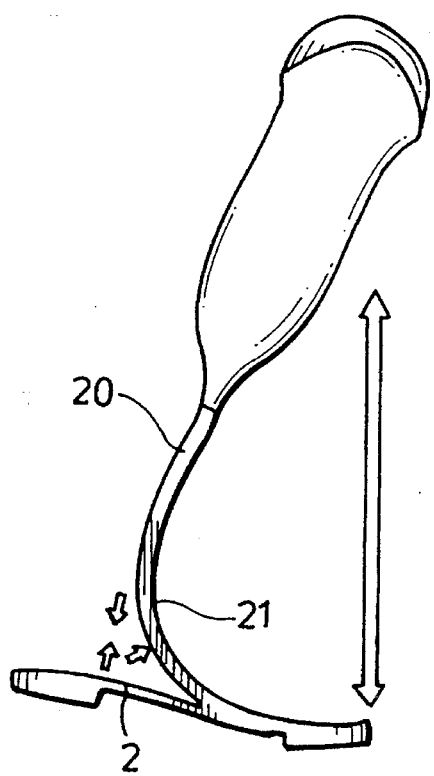
FIG. 3 illustrates how the conventional artificial foot of FIG. 2 results when in use.
Figure 4:
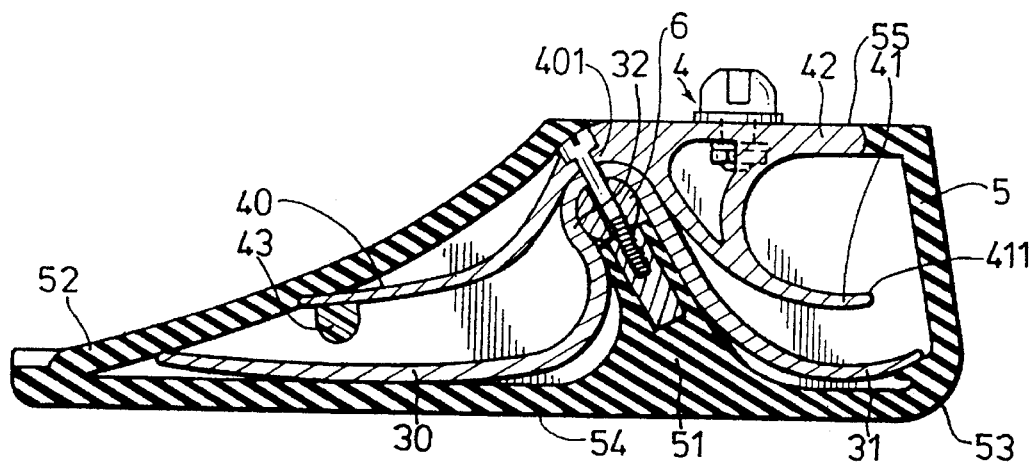
FIG. 4 shows a cross sectional view of a first preferred embodiment of an artificial foot of the present invention.
Figure 5:
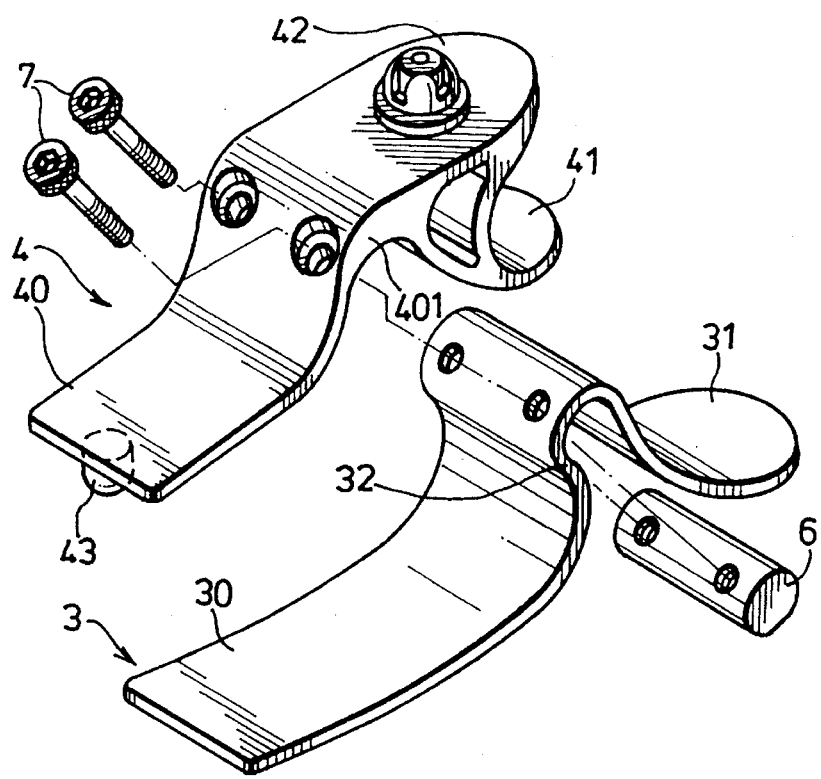
FIG. 5 shows an exploded view of the components which are installed in a foot-shaped casing of the artificial foot shown in FIG. 4.
Figure 6:
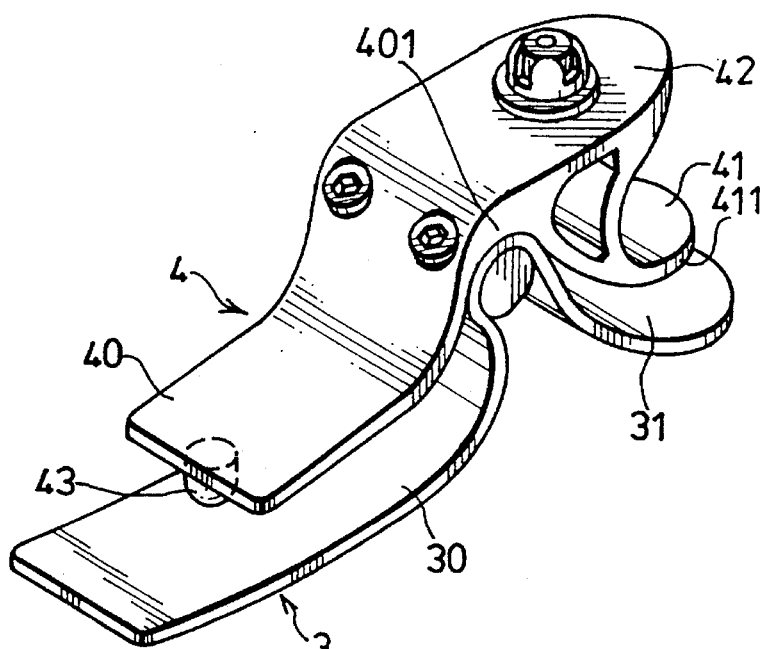
FIG. 6 is an assembled view of the components shown in FIG. 5.

Referring to FIGS. 4 and 5, an artificial foot of the present invention is shown to comprise a foot-shaped casing 5 which is made of an elastic and flexible material, such as plastic, and which has an open top 55, a closed bottom 54, a toe portion 52, a heel portion 53 and a positioning projection 51 that is formed within the foot-shaped casing 5 and that extends upwardly from the closed bottom 54.

A flexible muscle member 3 is disposed inside the foot-shaped casing 5 and includes an upwardly protruding curved section 32 mounted on the positioning projection 51, and first front and rear section 30, 31 which respectively extend forwardly and rearwardly from the curved intermediate curved section 32 into the toe and heel portions 52, 53 of the casing 5. In this embodiment, the muscle member 3 is a one-piece plate, the curved intermediate portion 32 is substantially folded, while the first front and rear sections 30, 31 are engaged with the toe and heel portions 52, 53 respectively.

A stop member 4 includes a weight bearing section 42 disposed on the foot-shaped casing 5 so as to cover the open top 55 of the same. The weight bearing section 42 is to be connected to the stump of an amputee and has an upwardly curved bottom part 401 superimposed on the curved intermediate section 32 of the muscle member 3. The stop member 4 has a second front section 40 which extends downwardly and frontwardly from the curved bottom part 401 into the toe portion 52 so as to dispose the same above the first front section 30 of the muscle member 3. The stop member 3 further has a second rear section 41 which extends from the curved bottom part 401 into a space between the weight bearing section 42 and the first rear section 31 of the muscle member 3. Under such a condition, the second rear section 41 of the stop member 4 is disposed above the first rear section 31 of the muscle member 3.

Figure 7:
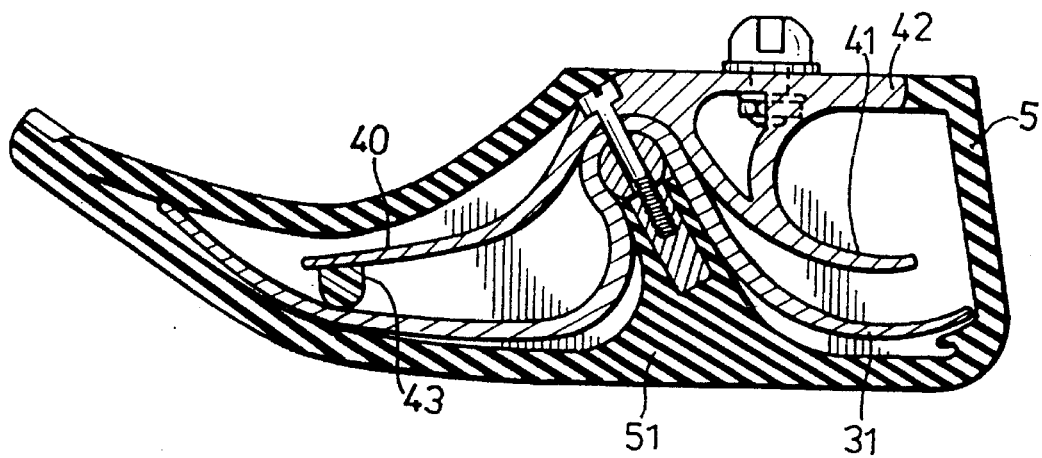
FIG. 7 illustrates the artificial foot of the present invention when in use.

Referring to FIG. 7, note that the stop member 4 has a substantial amount of rigidity so that when the amputee is at an upright position, the overall weight of the amputee is distributed evenly over the artificial foot. Under such a condition, the first front and rear sections 30, 31 of the muscle member 3 expand so as to abut with the closed bottom 54, thereby creating a larger contact area to support the amputee steadily. When the first front section 30 of the muscle member 3 is bent upwardly with respect to the stop member 4 due to a walking or running action, the upwardly bending action is prevented from bending further by the second front section 40 of the stop member 4. Thus, the likelihood of the amputee falling to the ground is minimized.

Figure 8:
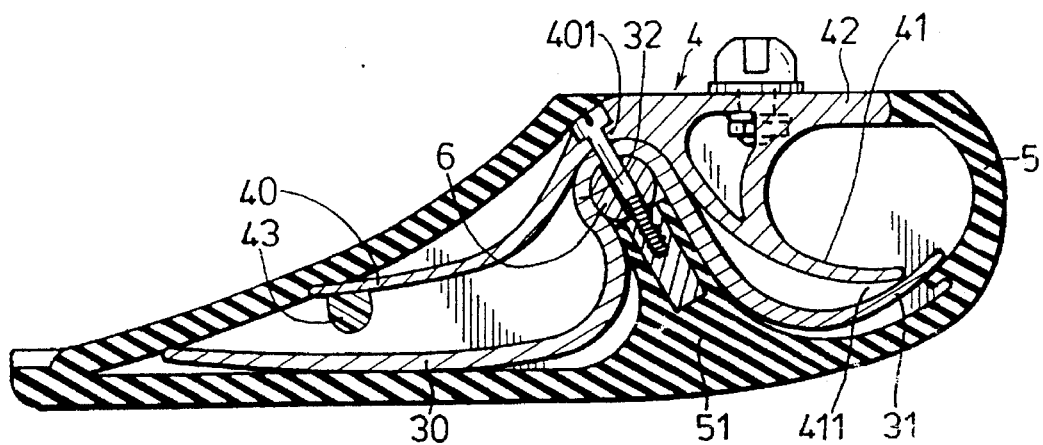
FIG. 8 is another illustration of the artificial foot of the present invention when in use.

Referring to FIG. 8, when the heel portion 53 is compressed, upwardly bending action of the first rear section 31 of the muscle member 3 is prevented from further bending by a free end 411 of the second rear section 41 of the stop member 4. Pivotal action of the muscle member 3 is thus limited within a range which can prevent the amputee from falling while walking or running with the use of the artificial foot of the present invention.

In this embodiment, the curved intermediate section 32 of the muscle member 3 is folded so as to be a semi-circular portion with a concave face and a convex face. A friction reducing piece 6, which is in the shape of a cylinder, is sandwiched within the folded semi-circular portion so that the friction reducing piece 6 is disposed between the concave face of the muscle member 3 and the positioning projection 51 to buffer the muscle member 3 and the positioning projection 51, thereby reducing wearability thereamong. Thus, the positioning projection 51 of the foot-shaped casing 5 is prevented from untimely ruin that is caused by constant pivotal action of the muscle member 3 relative to the positioning projection 51. The useful life of the artificial foot of the present invention can therefore be prolonged. In addition, the curved bottom part 401 of the stop member 4 has a curved inner surface abutting against the convex face of the folded semi-circular portion of the muscle member 3. Since the curved inner surface of the stop member 4 has a curvature smaller than that of concave face of the muscle member 3, the pivotal action of the muscle member 3 is facilitated.

A screw fastener 7 passes through the stop member 4 so as to extend through the curved bottom part 401, the curved intermediate section 32 of the muscle member 3, the friction reducing piece 6 and the positioning projection 51 in order to hold them securely at a proper position.

Figure 9:
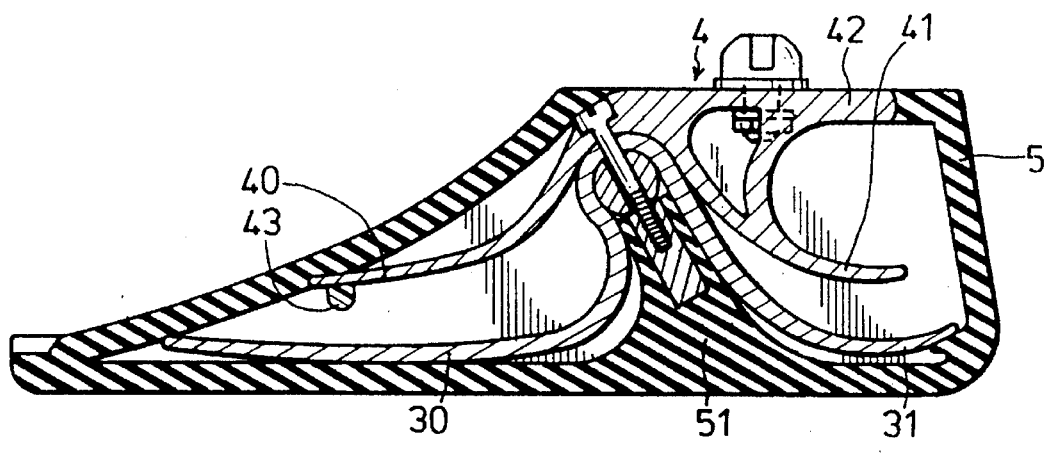
FIG. 9 shows a cross-sectional view of a second preferred embodiment of the artificial foot of the present invention.

The body weight of the amputee differs individually. To permit bending action while preventing the amputee from falling, an abutting spacer 43 is attached to the first front section 40 of the stop member 4 to abut against the first front section of the muscle member 3, thereby limiting a space therebetween. FIG. 9 shows another preferred embodiment of the artificial foot of the present invention. In this embodiment, an abutting spacer 43 with smaller size.

While a preferred embodiment has been described and explained, it will be apparent that many changes and modifications can be made in the general construction and arrangement of the present invention without departing from the scope and spirit thereof. Therefore, it is desired that the present invention be not limited to the exact disclosure but only to the extent of the appended claims.

I claim:

1. An artificial foot to be secured to the stump of an amputee comprising;

an elongated foot-shaped casing with an open top and a closed bottom, said foot-shaped casing having a toe portion, a heel portion and a positioning projection formed within said foot-shaped casing and extending substantially upward from the closed bottom;

a flexible muscle member provided inside said foot-shaped casing and including an upwardly protruding curved intermediate section riding on and mounted to said positioning projection, and first front and rear sections respectively extending forwardly and rearwardly from said curved intermediate section into said toe and heel portions, wherein said flexible muscle member is one-piece plate member, said curved intermediate section having a substantially semi-circular portion with a concave face and a convex face;

a stop member having weight bearing section covering said open top, said weight bearing section having an upwardly curved bottom part facing and being superimposed on said curved intermediate section of said flexible muscle member, a second front section extending from said curved bottom part downwardly and frontwardly into said toe portion so as to be disposed above said first front section of said flexible muscle member to prevent further bending movement of said first front section of said flexible muscle member relative to said second front section of said stop member when said first front section of said flexible muscle member is bent by application of pressure, said stop member further having a second rear section extending from said curved bottom part downwardly and rearwardly between said weight bearing section and said first rear section of said flexible muscle member to prevent further upward bending movement of said first rear section of said flexible muscle member when said first rear section of said flexible muscle member is bent by application of pressure on said heel portion.

2. The artificial foot as defined in claim 1, further comprising a cylindrical friction reducing piece provided between said concave face of said semi-circular portion of said curved intermediate section and said positioning projection, said curved bottom part of said stop member having a curved inner surface in contact with said convex face of said semi-circular portion.

3. The artificial foot as defined in claim 2, wherein said curved inner surface of said curved bottom part has a curvature that is smaller than that of said concave face of said semi-circular portion of said plate member.

4. The artificial foot as defined in claim 2, further comprising a screw fastener passing through said stop member so as to extend through said curved bottom part, said semi-circular portion of said flexible muscle member, said friction reducing piece and said positioning projection.

* * * * *